US012599609B2

(12) United States Patent
Gordon et al.

(10) Patent No.: US 12,599,609 B2
(45) Date of Patent: Apr. 14, 2026

(54) METHODS OF TREATING FUCHS ENDOTHELIAL CORNEAL DYSTROPHY AFTER DESCEMETORHEXIS

(71) Applicant: KOWA COMPANY, LTD., Nagoya (JP)

(72) Inventors: Gary Gordon, Morrisville, NC (US); Kazuhito Suehira, Boston, MA (US)

(73) Assignee: Kowa Company, Ltd., Nagoya (JP)

( * ) Notice: Subject to any disclaimer, the term of this patent is extended or adjusted under 35 U.S.C. 154(b) by 375 days.

(21) Appl. No.: 18/270,728

(22) PCT Filed: Jan. 20, 2022

(86) PCT No.: PCT/US2022/013045
§ 371 (c)(1),
(2) Date: Jul. 1, 2023

(87) PCT Pub. No.: WO2022/159533
PCT Pub. Date: Jul. 28, 2022

(65) Prior Publication Data

US 2024/0082256 A1 Mar. 14, 2024

Related U.S. Application Data

(60) Provisional application No. 63/139,993, filed on Jan. 21, 2021.

(51) Int. Cl.

| | |
|---|---|
| ***A61K 31/551*** | (2006.01) |
| ***A61K 31/4709*** | (2006.01) |
| ***A61K 31/573*** | (2006.01) |
| ***A61K 47/02*** | (2006.01) |
| ***A61K 47/10*** | (2017.01) |
| ***A61P 27/02*** | (2006.01) |

(52) U.S. Cl.
CPC ........ *A61K 31/551* (2013.01); *A61K 31/4709* (2013.01); *A61K 31/573* (2013.01); *A61K 47/02* (2013.01); *A61K 47/10* (2013.01); *A61P 27/02* (2018.01)

(58) Field of Classification Search
CPC .............................. A61K 31/551; A61P 27/02
See application file for complete search history.

(56) References Cited

U.S. PATENT DOCUMENTS

| | | | | |
|---|---|---|---|---|
| 9,248,125 | B2 | 2/2016 | Koizumi et al. | |
| 9,844,556 | B2 | 12/2017 | Honjo et al. | |
| 2013/0317049 | A1 | 11/2013 | Yum et al. | |
| 2016/0235665 | A1* | 8/2016 | Shah | A61K 9/0048 |
| 2017/0367977 | A1* | 12/2017 | Suzuki | A61K 31/4704 |

FOREIGN PATENT DOCUMENTS

| | | | |
|---|---|---|---|
| JP | 2007182438 | A * | 7/2007 |
| WO | 2020/174638 | A1 | 9/2020 |
| WO | 2020/175636 | A1 | 9/2020 |

OTHER PUBLICATIONS

Kowa Company, Ltd., International Application No. PCT/US2022/013045 filed Jan. 2, 200222; International Search Report and Written Opinion; ISA/US; Apr. 4, 2022; 14 pp.

Macsi et al.; Use of Topical Rho Kinase Inhibitors in the Treatment of Fuchs Dystrophy After Descemet Stripping Only, Cornea, May 1, 2019; vol. 38.; pp. 529-534.

Maloney et al.; Descemetorhexis Without Grafting for Fuchs Endothelial Dystrophy-Supplementation with Topical Ripasudil; Cornea, Apr. 14, 2017; vol. 36; pp. 642-648.

Blitzer et al.; Update on the Surgical Management of Fuchs Endothelial Corneal Dystrophy, Opthalmol Ther; https://doi.org/10.1007/s40123-020-00293-3; Aug. 25, 2020; 9 pp.

Borkar et al.; Treatment of Fuchs Endothelial Dystrophy by Descemet Stripping Without Endothelial Karatoplasty; Cornea; vol. 35, No. 10; Oct. 2016; 8 pp.

Okumura et al.; The New Therapeutic Concept of Using a Rho Kinase Inhibitor for the Treatment of Corneal Endothelial Dysfunction; Cornea; vol. 30; No. 10; Suppl. 1; Oct. 2011; 6 pp.

Iovieno et al.; Descemetorhexis Without Graft Placement for the Treatment of Fuchs Endothelial Dystrophy: Preliminary Results and Review of the Literature; Cornea; vol. 0; No. 0; Month 2017; 6 pp.

Garcerant et al.; Descemet's Stripping Without Endothelial Keratoplasty; Curr Opin Ophthalmol 2019, 30:000-000 DOI:10.1097/ICU.0000000000000579; 1040-8738; 11 pp.

The Soap and Detergent Association; Glycerine: an overview; Copyright 1990; Source: Bosart, L.W.. and Snoddy, A.O., Ind. Eng. Chem., 19,506-510 (1927); 27 pp.

Okimura et al; Effect of the Rho-Associated Kinase Inhibitor Eye Drop (Ripasudil) on Corneal Endothelial Wound Healing; iovs.arvojournals.org j ISSN: 1552-5783; IOVS; Mar. 2016; vol. 57; No. 3; 9 pp.

Okumura et al.; Application of Rho Kinase Inhibitors for the Treatment of Corneal Endothelial Diseases; Handawi; Journal of Opthalmology; vol. 2017, Article ID 2646904, https://doi.org/10.1155/2017/2646904; 8 pp.

Moloney et al.; 5-Year Outcomes of Descemet Stripping Only in Fuchs Dystrophy; Cornea; vol. 39; No. 8; Aug. 2020; 4 pp.

Moloney et al; Descemet Stripping Only Supplemented With Topical Ripasudil for Fuchs Endothelial Dystrophy 12-Month Outcomes of the Sydney Eye Hospital Study; Cornea; vol. 00; No. 00; Month 2020; 7 pp.

Moshirfar et al.; Use of Rho kinase Inhibitors in Ophthalmology: a Review of the Literature; Med. Hypothesis Discov. Innov. Ophthalmol. 2018; 7(3); 11 pp.

Moloney, Gregory; Moving beyond lamellar keratoplasty—Are we taking our first step?; Clinical and Experimental Vision and Eye Research (2018), 1, pp. 1-2.

Dalton et al.; ROCK inhibitors show promise in glaucoma treatment; Ophthalmology Times; Nov. 1, 2015; 4 pp.

(Continued)

*Primary Examiner* — James D. Anderson
(74) *Attorney, Agent, or Firm* — Clark G. Sullivan

(57) ABSTRACT

Methods for treating Fuchs endothelial corneal dystrophy ("FECD"), and medications that promote healing in FECD patients following descemetorhexis.

26 Claims, No Drawings

(56) References Cited

OTHER PUBLICATIONS

Kowa Company, Ltd.; Granatec ophthalmic solution 0.4%; Nov. 20, 2020; 97 pages.
Kowa Company, Ltd.; Granatec ophthalmic solution 0.4%; Nov. 20, 2020 79 pages—English Translation.
Price et al.; Randomized, double-masked, pilot study of netarsudil 0.02% ophthalmic solution for treatment of corneal edema in Fuchs dystrophy; American Journal of Ophthalmology (2021), doi: https://doi.org/10.1016/j.ajo.2021.03.006; 13 pp.
Okumura et al.; The ROCK Inhibitor Eye Drop Accelerates Corneal Endothelium Wound Healing; The Association for Research in Vision and Ophthalmology, Inc.; www.iovs.org j ISSN: 1552-5783; 2013; 10 pp.

* cited by examiner

METHODS OF TREATING FUCHS ENDOTHELIAL CORNEAL DYSTROPHY AFTER DESCEMETORHEXIS

FIELD OF THE INVENTION

The present invention relates to Fuchs endothelial corneal dystrophy ("FECD"), and medications that promote healing in FECD patients following descemetorhexis.

BACKGROUND

In Fuchs endothelial corneal dystrophy ("FECD"), there is an increased rate of loss of endothelial cells, starting in the center of Descemet's membrane and spreading to the periphery. There is an increased deposition of extracellular matrix on Descemet's membrane, resulting in excrescences known as guttae, which are a marker of the condition. Guttae may coalesce and inhibit the migration of endothelial cells. Eventually the corneal endothelium ceases to function effectively, and the cornea begins to cloud, leading eventually to blindness.

Currently, most patients undergoing keratoplasty for FECD have Stage 2 disease and the procedure starts with descemetorhexis, removing an area of the roughened and irregular Descemet's membrane (including the central guttae) from the diseased cornea. The excised area is replaced with a graft of endothelial cells: either donor Descemet's membrane with a thin layer of corneal stroma (Descemet stripping endothelial keratoplasty), or, increasingly commonly, donor Descemet's membrane alone (Descemet's membrane endothelial keratoplasty).

Experience with failed grafts has indicated that even though there is an underlying abnormality of endothelial cells in FECD, areas of stroma exposed by descemetorhexis can be re-endothelialised and the migrated endothelial cells can maintain corneal transparency. Mathematical modelling of the healing of an inadvertent 5 mm diameter descemetorhexis in an elderly man without FECD suggested that normal healing is achieved by a redistribution of peripheral endothelial cells into the central defect without any increase in the number of endothelial cells. This led to the proposal that some cases of FECD, particularly those with relatively preserved peripheral endothelial cells, can be treated by descemetorhexis alone.

There is a medical need for medication that can speed healing after descemetorhexis and that can help establish a high, functional endothelial cell density to maintain corneal transparency.

SUMMARY OF INVENTION

The present invention relates to novel methods for treating FECD with ripasudil and novel formulations thereof. Thus, in a first principal embodiment the invention provides a method of treating FECD affecting the Descemet membrane of a patient's cornea, in a patient in need thereof having a central corneal thickness less than 670 μm, comprising: (a) removing a central portion of the Descemet membrane from the patient's eye; and (b) topically administering to the patient's eye a therapeutically effective amount of ripasudil or a pharmaceutically acceptable salt thereof, from 2 to 4 times per day, for a therapeutically effective period of time.

In a second principal embodiment the invention provides a method of treating FECD affecting the Descemet membrane of a patient's cornea, in a patient in need thereof having a peripheral endothelial cell density less than 1000 cells per $mm^2$, comprising: (a) removing a central portion of the Descemet membrane from the patient's eye; and (b) topically administering to the patient's eye a therapeutically effective amount of ripasudil or a pharmaceutically acceptable salt thereof formulation for a therapeutically effective period of time.

In a third principal embodiment the invention provides a method of treating FECD affecting the Descemet membrane of a patient's cornea, in a patient in need thereof, comprising: (a) removing a central portion of the Descemet membrane from the patient's eye; and (b) topically administering to the patient's eye a therapeutically effective amount of ripasudil or a pharmaceutically acceptable salt thereof in a preservative-free liquid formulation for a therapeutically effective period of time.

In a fourth principal embodiment the invention provides a method of treating FECD affecting the Descemet membrane of a patient's cornea, comprising: (a) removing a central portion of the Descemet membrane from the patient's eye; and (b) topically administering to the patient's eye a therapeutically effective amount of ripasudil or a pharmaceutically acceptable salt thereof from 1 to 3 times per day for a therapeutically effective period of time.

In a fifth principal embodiment the invention provides a method of treating FECD affecting the Descemet membrane of a patient's cornea, comprising: (a) removing a central portion of the Descemet membrane from the patient's eye; (b) topically administering to the patient's eye a therapeutically effective amount of ripasudil or a pharmaceutically acceptable salt thereof for from 8 to 12 weeks; and (c) tapering the therapeutically effective amount to zero over approximately two weeks.

In a sixth principal embodiment the invention provides a method of reducing corneal edema in a patient treated for Fuchs Endothelial Corneal Dystrophy ("FECD") in a patient in need thereof, comprising (a) removing a central portion of the Descemet membrane from the patient's eye; and (b) topically administering to the patient's eye a therapeutically effective amount of ripasudil or a pharmaceutically acceptable salt thereof for a therapeutically effective period of time.

In a seventh principal embodiment the invention provides a preservative-free liquid solution of ripasudil hydrochloride comprising: (a) from 0.3% (w/v) to 0.5% (w/v) ripasudil hydrochloride, based on the weight of the free base of ripasudil excluding any waters of hydration; (b) an optional pH buffer; (c) from 1.5% (w/v) to 2.0% (w/v) glycerol; (d) sodium hydroxide q.s. to a pH of from 4 to 7.5; and (e) purified water q.s. to 100%.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Definitions and Use of Terms

As used in this specification and in the claims which follow, the singular forms "a," "an" and "the" include plural referents unless the context clearly dictates otherwise.

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality components, steps or conditions, it will be understood that the element can also be described as comprising any combination of such plurality, or "consisting of" or "consisting essentially of" the plurality or combination of components, steps or conditions.

"Approximately," "about," "ca.," and terms of like import, when used to describe concentrations of components of a formulation, allow for variations in the recited concentrations that remain within the United States FDA's requirements for a formulation that is qualitatively (Q1) and quantitatively (Q2) the same as a reference formulation. I.e., unless otherwise specified, the term refers to a +/−5% difference in the recited concentration. However, it will be understood that the invention is not limited to +/−5% variability in the recited concentrations for a particular formulation. Thus, "approximately," "about," "ca.," and terms of like import can also be substituted with +1-12%, or +/−10%, +/−7%, +/−3%, or +/−1%.

"Therapeutically effective amount" means that amount which, when administered to a human for supporting or affecting a metabolic process, or for treating or preventing a disease, is sufficient to cause such treatment or prevention of the disease, or supporting or affecting the metabolic process.

When ranges are given by specifying the lower end of a range separately from the upper end of the range, or specifying particular numerical values, it will be understood that a range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

When "drug therapy" is recited, it will be understood that the therapy can be accomplished through any suitable route of administration using any acceptable dosage form, and that the drug can be administered as the free base, a salt, or an ester or other prodrug moiety.

In the context of the present invention insofar as it relates to any of the disease conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denote to arrest, delay the onset (i.e., the period prior to clinical manifestation of a disease) and/or reduce the risk of developing or worsening a disease.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

Ripasudil, a derivative of fasudil, is a rho kinase inhibitor drug marketed in Japan as Glanatec® for the treatment of glaucoma and ocular hypertension. The compound has the following chemical structure:

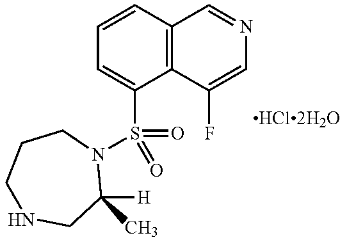 [SMILES: C[C@H]1CNCCCN1S(=O)(=O)c1cccc2cncc(F)c12]

and is present in the preferred solutions of the present invention as a hydrochloride salt, more preferably the dihydrate hydrochloride salt.

When the term "ripasudil" is used herein, without any further qualifier, it will be understood to refer to ripasudil free base or any pharmaceutically acceptable salt or hydrate thereof, in any pharmaceutically acceptable crystalline or amorphous form. However, it will not be understood to refer to a racemic mixture of ripasudil with its corresponding optical isomer. Rather, the term "ripasudil" refers to an optically pure isomer.

When a concentration of ripasudil, ripasudil hydrochloride, or ripasudil hydrochloride dihydrate are expressed herein, it will be understood that the concentration is based on the weight of the anhydrous ripasudil free base, without considering the contributing weight of the hydrochloride ion or any waters of hydration, unless stated expressly to the contrary.

When treatment benefits are expressed in terms of established testing protocols, it will be understood that the protocol used to evaluate benefit will be that version of the protocol in effect as of the earliest priority date for this application (i.e. Jan. 21, 2021).

Principal Embodiments

In a first principal embodiment the invention provides a method of treating FECD affecting the Descemet membrane of a patient's cornea, in a patient in need thereof having a central corneal thickness less than 670 μm, comprising: (a) removing a central portion of the Descemet membrane from the patient's eye; and (b) topically administering to the patient's eye a therapeutically effective amount of ripasudil or a pharmaceutically acceptable salt thereof, from 2 to 4 times per day, for a therapeutically effective period of time.

In a second principal embodiment the invention provides a method of treating FECD affecting the Descemet membrane of a patient's cornea, in a patient in need thereof having a peripheral endothelial cell density less than 1000 cells per $mm^2$, comprising: (a) removing a central portion of the Descemet membrane from the patient's eye; and (b) topically administering to the patient's eye a therapeutically effective amount of ripasudil or a pharmaceutically acceptable salt thereof formulation for a therapeutically effective period of time.

In a third principal embodiment the invention provides a method of treating FECD affecting the Descemet membrane of a patient's cornea, in a patient in need thereof, comprising: (a) removing a central portion of the Descemet membrane from the patient's eye; and (b) topically administering to the patient's eye a therapeutically effective amount of ripasudil or a pharmaceutically acceptable salt thereof in a preservative-free liquid formulation for a therapeutically effective period of time.

In a fourth principal embodiment the invention provides a method of treating FECD affecting the Descemet membrane of a patient's cornea, comprising: (a) removing a central portion of the Descemet membrane from the patient's eye; and (b) topically administering to the patient's eye a therapeutically effective amount of ripasudil or a pharmaceutically acceptable salt thereof from 1 to 3 times per day for a therapeutically effective period of time.

In a fifth principal embodiment the invention provides a method of treating FECD affecting the Descemet membrane of a patient's cornea, comprising: (a) removing a central portion of the Descemet membrane from the patient's eye; (b) topically administering to the patient's eye a therapeutically effective amount of ripasudil or a pharmaceutically acceptable salt thereof for from 8 to 12 weeks; and (c) tapering the therapeutically effective amount to zero over approximately two weeks.

In a sixth principal embodiment the invention provides a method of reducing corneal edema in a patient treated for Fuchs Endothelial Corneal Dystrophy ("FECD") in a patient in need thereof, comprising (a) removing a central portion of the Descemet membrane from the patient's eye; and (b) topically administering to the patient's eye a therapeutically effective amount of ripasudil or a pharmaceutically acceptable salt thereof for a therapeutically effective period of time.

Any of the first through sixth principal embodiments is preferably practiced by the administration of a 0.4% (w/v) solution of ripasudil or a pharmaceutically acceptable salt thereof either 2 or 4 times per day.

In any of the first through sixth principal embodiments, the ripasudil or pharmaceutically acceptable salt thereof is preferably first administered after step (a), and no later than 24 hours after step (a).

The ripasudil can also be supplemented by an antibiotic and/or a steroid. Thus, in any of the first through sixth principal embodiments, the method will preferably further comprise after step (a) topically administering to the treated eye a broad-spectrum antibiotic, preferably 0.5% moxifloxacin hydrochloride and a glucocorticoid, preferably 1% prednisolone acetate.

In any of the first through sixth principal embodiments step (a), the descemetorhexis procedure, will preferably comprise removing from 4.5 to 5.5 mm of the central portion of the Descemet membrane from the patient's eye.

In a seventh principal embodiment the invention provides a preservative-free liquid solution of ripasudil hydrochloride comprising: (a) from 0.3% (w/v) to 0.5% (w/v) ripasudil hydrochloride, based on the weight of the free base of ripasudil excluding any waters of hydration; (b) an optional pH buffer; (c) from 1.5% (w/v) to 2.0% (w/v) glycerol; (d) sodium hydroxide q.s. to a pH of from 4 to 7.5; and (e) purified water q.s. to 100%.

Patients Particularly Suitable for Treatment

The methods of the current invention can be further characterized based on various characteristics of the patient being treated. Thus, any of the second through sixth principal embodiments can be practiced in individuals having a treated eye with central corneal thickness less than 720, 700, 685, or 670 μm before the treatment. Any of the first through sixth principal embodiments can be practiced in individuals having a central corneal thickness less than 660, 640, 620, or even 600 μm.

The individual being treated also can be characterized by the peripheral endothelial cell density of the treated eye before treatment. Thus, in any of the first and third through sixth principal embodiments, the patient can have a peripheral endothelial cell density less than 2000, 1500, 1250, or 1000 cells per $mm^2$. In any of the first through sixth principal embodiments the patient can have a peripheral endothelial cell density less than 950, 900, 850, 800, or 750 cells per $mm^2$.

The individual being treated also can be characterized by the central guttae in the eye being treated. Thus, in any of the first through sixth principal embodiments, the method will preferably be practiced in an eye comprising confluent central guttae that can be removed by descemetorhexis of a circular area of 5 mm diameter or less.

The individual also can be characterized by the peripheral guttae in the eye being treated. Thus, in any of the first through sixth principal embodiments, the method will preferably be practiced in an eye that does not comprise confluent peripheral guttae outside a circular area of 5.5 mm diameter or less.

Drug Administration

In any of the first through sixth principal embodiments of the present invention, the drug is preferably administered dropwise, and is preferably administered as one drop per administration. The drug can be administered at various daily frequencies, but preferably is administered from 2 to 6 times daily, from 2 to 5 times daily, from 2 to 4 times daily, or simply 2, 3, or 4 times daily.

The length of administration also can vary. Thus, in any of the first through sixth principal embodiments, the drug can be administered from 4 to 26 weeks, from 6 to 20 weeks, or from 8 to 16 weeks, or simply 4 weeks, 6 weeks, 8 weeks, 10 weeks, 12 weeks, 14 weeks, or 16 weeks.

An additional tapering period can be added to any of the foregoing lengths of administration, during which the dose is decreased over a period of from 1 to 4 weeks, preferably 2 weeks. During this "tapering phase," the dose of the drug can be reduced in a stepwise fashion, or alternatively, the dose can simply be cut in ½ during this tapering phase, and reduced to zero at the end of the tapering phase.

Therapeutic Endpoints

Various endpoints can be used to evaluate the effectiveness of the methods of the current invention.

Thus, in one subembodiment, applicable to any of the first through sixth principal embodiments, the treatment comprises increasing central endothelial cell density in the treated eye, relative to an untreated control subject who has undergone descemetorhexis, by 10%, 20%, or even 30%.

In another subembodiment, applicable to any of the first through sixth principal embodiments, the treatment comprises increasing peripheral endothelial cell density in the treated eye by 10%, 20%, or even 30%.

In another subembodiment, applicable to any of the first through sixth principal embodiments, the treatment comprises decreasing central corneal thickness in the treated eye by 10%, 20%, or even 30%.

In another subembodiment, applicable to any of the first through sixth principal embodiments, the treatment comprises increasing corneal clarity in the treated eye.

In another subembodiment, applicable to any of the first through sixth principal embodiments, the treatment comprises decreasing corneal stromal edema in the treated eye;

Thus, in another subembodiment, applicable to any of the first through sixth principal embodiments, the treatment comprises increasing visual acuity in the treated eye; and Thus, in another subembodiment, applicable to any of the first through sixth principal embodiments, the treatment comprises increasing visual contrast sensitivity in the treated eye.

In still another embodiment, applicable to any of the first through sixth embodiments, the treatment comprises reducing glare in the treated eye.

In another embodiment, applicable to any of the first through sixth embodiments, the treatment comprises preventing or delaying corneal transplant surgery.

The treatment has demonstrated particular benefit improving central corneal endothelial corneal density ("ECD"), best corrected visual acuity ("BCVA"), and reduction of corneal edema, using BID and QID dosing of a 0.4% ripasudil hydrochloride formulation.

Formulations of the Present Invention

In general, any pharmaceutically acceptable solution of ripasudil, at a concentration of from 0.1 to 1.0% (w/v) ripasudil, is suitable for practicing the methods of the current invention. Preferably, the solution is free of preservatives such as benzalkonium chloride. A preferred concentration of ripasudil is from 0.2 to 0.5% (w/v) or approximately 0.4% (w/v) in the solution.

A preferred formulation will be preservative-free, and will further comprise glycerin, sodium dihydrogen phosphate and sodium hydroxide at a pH of from about 5 to about 7. The sodium dihydrogen phosphate can be hydrated or anhydrous, but in a preferred embodiment is the dihydrate. The glycerin can be biologically derived or synthetic, and may comprise up to 20% (v/v) water when added to the formulation, but is preferably synthetic and preferably comprises less than 1%, 0.5%, or 0.1% (v/v) water when added to the formulation. If water is present in the glycerin when added to the formulation, it will be understood that the water is not used in any of the calculations of glycerin concentration used in this document.

Pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of pharmaceutical compositions can be adjusted according to routine skills in the art. See Goodman and Gilman's, The Pharmacological Basis for Therapeutics (7th ed.).

In a preferred embodiment, the formulation used in the methods of the current invention is the same formulation that constitutes the seventh principal embodiment of the present invention. Thus, in a preferred embodiment, the methods of the present invention are practiced with a preservative-free liquid solution of ripasudil hydrochloride comprising: (a) from 0.3% (w/v) to 0.5% (w/v) ripasudil hydrochloride, based on the weight of the free base of ripasudil excluding any waters of hydration; (b) an optional pH buffer; (c) from 1.5% (w/v) to 2.0% (w/v) glycerol; (d) sodium hydroxide q.s. to a pH of from 4 to 7.5; and (e) purified water q.s. to 100%.

This preferred formulation can be more particularly characterized based on various parameters. Thus, in one subembodiment the formulation comprises from 0.35% (w/v) to 0.45% (w/v) ripasudil hydrochloride, based on the weight of the free base of ripasudil excluding any waters of hydration. In another subembodiment the formulation comprises from 0.35% (w/v) to 0.45% (w/v) sodium dihydrogen phosphate, excluding any waters of hydration;

A particularly preferred formulation comprises (a) approximately 0.4% (w/v) ripasudil hydrochloride, based on the weight of the free base of ripasudil excluding any waters of hydration; (b) approximately 0.4% (w/v) sodium dihydrogen phosphate, excluding any waters of hydration; (c) approximately 1.77% (w/v) glycerol; (d) sodium hydroxide q.s. to a pH of from 5 to 7; and (e) purified water q.s. to 100%.

Any of the foregoing embodiments or subembodiments can be further characterized by comprising: (a) approximately 0.49 g/100 mL ripasudil hydrochloride dihydrate; (b) approximately 0.52 g/100 mL sodium dihydrogen phosphate dihydrate; (c) the absence of any preservatives, anti-oxidants, or chelating agents; (d) the absence of benzalkonium chloride; and/or (e) any combination thereof.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Optimized Ripasudil Eye Drop Formulation for the Treatment of Patients with Fuchs Endothelial Corneal Dystrophy A suitable formulation for treating patients with Fuchs Endothelial Corneal Dystrophy following descemetorhexis is provided in Table 1. This formulation is sometimes referred to hereinafter as K-321.

TABLE 1

| Ingredient | Purpose | Concentration |
|---|---|---|
| Active constituent | | |
| Ripasudil hydrochloride dihydrate | | 0.4896 g/100 mL* |
| Other constituents | | |
| Sodium dihydrogen phosphate dihydrate | Buffer | 0.52 g/100 mL** |
| Glycerol 100% | Tonicity Agent | 1.769 g/100 mL |
| Sodium hydroxide | pH regulator | q.s. to pH 5-7 |
| Purified Water | Solvent | q.s. to 100% |

*Equivalent to 0.4 mg/100 ml based on weight of anhydrous free base of ripasudil

**Equivalent to 0.4 mg/100 mL based on weight of anhydrous sodium dihydrogen phosphate

Example 2. Descemetorhexis of the Study Eye

As a condition of participating in the clinical study described in Example 3, each patient will undergo descemetorhexis of a study eye selected by the investigator for surgery. A digital photo of the study eye is taken immediately before and immediately after the descemetorhexis. The investigator will perform descemetorhexis to remove central confluent guttae, removing an area of Descemet membrane with a diameter of 4.5 to 5.5 mm. The longest diameter and the shortest diameter must be recorded. Detailed procedures for performing descemetorhexis are described in several literature references, including, for example, Macsai M S, Shiloach M. Cornea. 2019; 38:529-534, and Moloney G, Congote D G, Hirnschall N, et al. Cornea. 2020 Jul. 31. doi: 10.1097/ICO.0000000000002437. Online ahead of print.

Recommended post-descemetorhexis concomitant therapy consists of broad spectrum antibiotic (0.5% moxifloxacin hydrochloride) instilled at least once daily for 1 week and glucocorticoid (1% prednisolone acetate) instilled 3 times daily for the first 7 days, followed by once daily for the next 7 days, and terminated thereafter. The investigator may add antibiotic and glucocorticoid dosing after this 14 days as rescue therapy if the investigator judges it necessary. When more than 1 different eye drop is administered (including study drug), the study drug must be administered first, followed by any non-study eye drop (after at least 5 minutes have passed).

Example 3. A Double Masked, Randomized, Placebo Controlled, Parallel Group, 12 Week, Phase 2 Study to Investigate the Safety and Efficacy of Ripasudil Eye Drops After Descemetorhexis in Patients with Fuchs Endothelial Corneal Dystrophy In this U.S. FDA approved study, the primary objective is to investigate the effect of K-321 dosed for 12 weeks on central ECD in patients with FECD after descemetorhexis. Secondary and exploratory objectives of this study include (i) investigating the effect of K-321 on central ECD, corneal thickness, and corneal clarity in patients with FECD at each visit after descemetorhexis out to 52 weeks, (ii) assessing the safety and tolerability of K-321 in patients with FECD at each visit after descemetorhexis out to 52 weeks, and (iii) investigating the effect of K-321 on visual acuity, visual contrast sensitivity, corneal morphology, and vision related quality of life.

Study Design:

This is a multi-centre, double-masked, randomised, parallel-group, placebo-controlled, 2-period study of patients with FECD after descemetorhexis.

The first period is the treatment period, consisting of a screening visit within a 1- to 4-week screening period, a descemetorhexis and randomisation visit, a 12-week full treatment period containing 7 interim visits (including 1 optional visit at Week 2) and an end-of-treatment (EOT) visit scheduled for Week 12. During the 2 weeks immediately following the EOT visit, each enrolled patient will taper dosing of study drug to zero.

The second period is a follow-up observation period of 40 weeks, including the tapering phase and containing 4 interim visits and an end-of-study (EOS) visit. Patients are not to self-administer study drug after approximately Week 14. Patients will be considered to have completed the study with the completion of their EOS visit (scheduled for Week 52).

There are 3 treatment groups: K-321 ophthalmic solution 0.4% dosed 4 times daily (QID); K-321 ophthalmic solution 0.4% dosed 2 twice daily (BID); and placebo. After obtaining informed consent at Visit 1, the investigator will select one eye as the study eye and the patient will come back for the descemetorhexis operation and random assignment to treatment after 1 to 4 weeks (Visit 2). At Visit 2, each patient's eligibility for study participation will be confirmed, including a successful descemetorhexis operation that meets the inclusion criteria.

After eligibility is confirmed, patients will be randomly assigned to the 3 treatment groups (in a 1:1:1 ratio). All patients will be instructed to apply the study drug only to the study eye.

Except on days of study visits on Day 1 through Week 12 (not including Visit 9) during the treatment period, study drug will be dosed by the patient 4 times per day: morning, mid-day, evening, and night. Each patient will be provided with 2 sets of color-coded ampoule pouches, one set to be applied morning and night (M/N) and the other to be applied mid-day and evening (MD/E).

On study visit days Visit 3 through Visit 9, patients will not apply any study drug until after all study measurements have been completed; thereafter on those days, patients will start dosing with the dose closest in timing to the dosing regimen and continue with the remaining doses for the day. Additionally, on Visit 3 they must first apply study drug after the end of the descemetorhexis procedure on Day-1(Visit2).

At Visit 9 (Week 12), patients will enter the drug-tapering phase of the follow-up period, and new study drug will be dispensed.

During the follow up period, patients will attend 5 study visits, starting at Week 16 (Visit 10). A central corneal image analysis reading centre (CIARC) will determine central ECD by analysing digital images of the corneal endothelium.

Main Inclusion Criteria:

Each patient must meet all of the following criteria to be enrolled in this study:

1. Is at least 18 years old at the screening visit.
2. Has a diagnosis of FECD.
3. Has confluent central guttae in the study eye that can be removed by descemetorhexis of a circular area of 5 mm diameter or less.
4. Has a study eye with best corrected visual acuity BCVA of 75 letters or fewer by Early Treatment Diabetic Retinopathy Study ETDRS testing (Snellen equivalent of 20/32 or worse).
5. The study eye descemetorhexis is confirmed to have excised a central area with confluent guttae and a diameter of 4.5 to 5.5 mm.

Main Exclusion Criteria:

Patients meeting any of the following criteria will be excluded from the study:

1. Is a female patient pregnant or at risk of becoming pregnant.
2. Has a study eye with confluent guttae in the periphery or confluent guttae outside the stripped area (individual guttae are allowed).
   Note that patients may have individual or small number of guttae remaining outside the stripped area, but there should be no areas of confluent guttae remaining after the descemetorhexis. For example, a patient who had 5 to 10 guttae remaining in a few spots around the circumference of the descemetorhexis would not be excluded by this criterion.
3. Has a study eye with a history of cataract surgery within 90 days, prior ocular surgery other than cataract, or plans to receive any surgical treatment on the study eye during study.
4. Plans to receive any surgical treatment for FECD or cataract on the non-study eye, or has had ocular surgery in the non-study eye within 30 days.
5. Has advanced corneal stromal oedema defined as the presence of widespread haze or bullae on slit lamp examination.
6. Has a study eye with central corneal thickness ≥670 μm.
7. Has known severe comorbidities that may interfere with descemetorhexis (e.g., a bacterial, viral, or fungal ophthalmic infection).

Efficacy Assessments:

Efficacy assessments include corneal ECD, corneal thickness, corneal oedema, corneal morphology, BCVA, contrast sensitivity, and the Visual Function Questionnaire 25 (VFQ 25).

Safety Assessments:

Safety assessments include the identification of AEs ocular safety assessments of both eyes (including slit lamp examination without pupil dilation to evaluate the condition of the lids, conjunctiva, anterior chamber, and cornea; intra ocular pressure measurement; and ocular examination with pupil dilation using an indirect ophthalmoscope according to the current standard of practice to evaluate the condition of the vitreous, macula, retina, optic nerve, choroid, and retinal periphery); vital sign measurements; and laboratory examinations.

Study Drug, Dosage, and Route of Administration:

Study drug is either K-321 ophthalmic solution containing ripasudil 0.4% (K-321 0.4%) or matching placebo. The K-321 treatments will comprise either BID or QID dosing of K-321.

Sample Size:

Approximately 60 patients will be enrolled in the study. 20 patients will be randomly assigned to each group.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating Fuchs Endothelial Corneal Dystrophy ("FECD") affecting the Descemet membrane of a patient's cornea, in a patient in need thereof, comprising:
- a) removing a central portion of the Descemet membrane from the patient's eye;
- b) topically administering to the patient's eye a therapeutically effective amount of ripasudil or a pharmaceutically acceptable salt thereof, from 2 to 4 times per day, for from 8-12 weeks; and
- c) tapering the therapeutically effective amount to zero over approximately two weeks.

2. A method of treating Fuchs Endothelial Corneal Dystrophy ("FECD") affecting the Descemet membrane of a patient's cornea, comprising:
- a) removing a central portion of the Descemet membrane from the patient's eye; and
- b) topically administering to the patient's eye a therapeutically effective amount of ripasudil or a pharmaceutically acceptable salt thereof for from 8 to 12 weeks;
- c) tapering the therapeutically effective amount to zero over approximately two weeks.

3. The method of claim 1, wherein the patient has a central corneal thickness less than 670 μm.

4. The method of claim 1, wherein the patient has a peripheral endothelial cell density less than 1000 cells per $mm^2$.

5. The method of claim 1, wherein the ripasudil or pharmaceutically acceptable salt thereof is administered in a preservative-free liquid formulation.

6. The method of claim 1, wherein the ripasudil or a pharmaceutically acceptable salt thereof is administered 4 times per day.

7. The method of claim 1, wherein the ripasudil or pharmaceutically acceptable salt thereof is administered for approximately 12 weeks.

8. The method of claim 1, wherein the ripasudil or pharmaceutically acceptable salt thereof is administered as a formulation comprising about 4 mg/mL ripasudil hydrochloride based on the weight of the free base and excluding any hydration.

9. The method of claim 1, wherein the ripasudil or pharmaceutically acceptable salt thereof is administered as a formulation comprising glycerin, sodium dihydrogen phosphate and sodium hydroxide at a pH of from about 5 to about 7.

10. The method of claim 1, wherein the ripasudil or pharmaceutically acceptable salt thereof is first administered after step (a), and no later than 24 hours after step (a).

11. The method of claim 1, wherein step (a) comprises removing from 4.5 to 5.5 mm of the central portion of the Descemet membrane from the patient's eye.

12. The method of claim 1, wherein the treatment comprises increasing visual acuity in the treated eye.

13. The method of claim 1, wherein the therapeutically effective amount of ripasudil or a pharmaceutically acceptable salt thereof is administered as a preservative-free liquid solution of ripasudil hydrochloride comprising:
- a) from 0.3% (w/v) to 0.5% (w/v) ripasudil hydrochloride, based on the weight of the free base of ripasudil excluding any waters of hydration;
- b) an optional pH buffer;
- c) from 1.5% (w/v) to 2.0% (w/v) glycerol;
- d) sodium hydroxide q.s. to a pH of from 4 to 7.5; and
- e) purified water q.s. to 100%.

14. The method of claim 13 wherein the solution comprises from 0.35% (w/v) to 0.45% (w/v) sodium dihydrogen phosphate, excluding any waters of hydration.

15. The method of claim 13 wherein the solution comprises:
- a) approximately 0.4% (w/v) ripasudil hydrochloride, based on the weight of the free base of ripasudil excluding any waters of hydration;
- b) approximately 0.4% (w/v) sodium dihydrogen phosphate, excluding any waters of hydration;
- c) approximately 1.77% (w/v) glycerol;
- d) sodium hydroxide q.s. to a pH of from 5 to 7; and
- e) purified water q.s. to 100%.

16. The method of claim 13, wherein the solution comprises:
- a) approximately 0.49 g/100 mL ripasudil hydrochloride dihydrate; and/or
- b) approximately 0.52 g/100 mL sodium dihydrogen phosphate dihydrate.

17. The method of claim 13, wherein the solution lacks any preservatives, anti-oxidants, or chelating agents.

18. The method of claim 13, wherein the solution lacks benzalkonium chloride.

19. The method of claim 1, wherein the ripasudil or a pharmaceutically acceptable salt thereof is administered 4 times per day for approximately 12 weeks.

20. The method of claim 1, wherein the ripasudil or a pharmaceutically acceptable salt thereof is administered 4 times per day for approximately 12 weeks in a formulation comprising about 4 mg/mL ripasudil hydrochloride based on the weight of the free base and excluding any hydration.

21. A method of treating Fuchs Endothelial Corneal Dystrophy ("FECD") affecting the Descemet membrane of a patient's cornea, comprising:

a) removing a central portion of the Descemet membrane from the patient's eye; and b) topically administering to the patient's eye a therapeutically effective amount of ripasudil hydrochloride, in a concentration of about 0.4 mg/mL based on the weight of the free base excluding any hydration, in the absence of any preservatives, four times per day, for from 8 to 12 weeks;

c) tapering the therapeutically effective amount to zero over approximately two weeks.

22. The method of claim 21, comprising administering the therapeutically effective amount of ripasudil hydrochloride for 12 weeks.

23. The method of claim 21, wherein the patient has a central corneal thickness less than 670 μm.

24. The method of claim 21, wherein the patient has a peripheral endothelial cell density less than 1000 cells per $mm^2$.

25. The method of claim 22, wherein the patient has a central corneal thickness less than 670 μm.

26. The method of claim 22, wherein the patient has a peripheral endothelial cell density less than 1000 cells per $mm^2$.

* * * * *